United States Patent [19]

Luoma et al.

[11] Patent Number: 4,735,081
[45] Date of Patent: Apr. 5, 1988

[54] METHOD AND APPARATUS FOR DETECTING PRESENCE AND CONCENTRATION OF VAPORS IN GASEOUS FLUIDS

[75] Inventors: Gregory A. Luoma, Victoria; Lannie K. Yee, Saanichton; Barrie D. Turnham, Victoria, all of Canada

[73] Assignee: Her Majesty the Queen in right of Canada as represented by the Minister of National Defence, Ottawa, Canada

[21] Appl. No.: 827,057

[22] Filed: Feb. 7, 1986

[30] Foreign Application Priority Data

Feb. 12, 1985 [CA] Canada .................................. 474141

[51] Int. Cl.⁴ ............................................ G01N 27/00
[52] U.S. Cl. ........................................................ 73/23
[58] Field of Search ............................................ 73/23

[56] References Cited

U.S. PATENT DOCUMENTS

| 3,431,770 | 3/1969 | Sanford et al. | 73/23 |
| 3,879,992 | 4/1975 | Bartera | 73/23 X |
| 4,116,042 | 9/1978 | Jenkins et al. | 73/23 |
| 4,446,720 | 5/1984 | Sinclair | 73/23 |
| 4,485,666 | 12/1984 | Higgins et al. | 73/23 |
| 4,561,286 | 12/1985 | Sekler et al. | 73/23 |

Primary Examiner—Stewart J. Levy
Assistant Examiner—Joseph W. Roskos
Attorney, Agent, or Firm—Cushman, Darby & Cushman

[57] ABSTRACT

A method of determining the concentration of a vapor in a gaseous fluid comprises the steps of passing a sample of the fluid through a channel having a crystal oscillator therein coated with a substance which absorbs the vapor, monitoring the deviation of the frequency of the oscillator from a base-line frequency representative of a fluid sample having a zero concentration of the vapor and converting the frequencydeviation, if any, to a numerical value indicative of the concentration of the vapor in the fluid.

20 Claims, 5 Drawing Sheets

METHOD AND APPARATUS FOR DETECTING PRESENCE AND CONCENTRATION OF VAPORS IN GASEOUS FLUIDS

The present invention relates in general to a method and apparatus for detecting the presence and concentration of vapours in a gaseous fluid and, more specifically, to a method and apparatus for detecting the presence and concentration of Otto fuel in ambient air.

BACKGROUND OF THE INVENTION

Propylene glycol dinitrate (PGDN), commonly referred to as "Otto Fuel II", is a liquid propellant used in most torpedoes. It must be handled in all servicing shops and presents a potential health hazard to workers exposed to it. Individuals exposed to concentrations in the order of 0.1-1.0 ppm of Otto Fuel II may experience symptoms such as headache, burning sensations in the eyes and loss of motor coordination while individuals exposed to higher concentrations may experience symptoms such as changes in blood hemoglobin to metheglobin, vasodilation and liver injury. Canada has adopted a threshold Limit Value (TLV) of 0.02 ppm, although experimental evidence suggests that a more reasonable level would be about 0.1 ppm.

While various attempts have been made, there has not been developed any device capable of continuously monitoring Otto Fuel II at a concentration level of 0.02 ppm. The ideal Otto Fuel II monitor must possess a number of desirable characteristics. First, the device must be small and light so that it can be readily moved to a site of possible contamination. It should also include an attached probe to spot check torpedoes and surfaces suspected of contamination. Second, the device must be sensitive, selective and stable. Since the monitor must be on continuously in an environment which may be contaminated with other chemicals, the detector must be highly selective for Otto Fuel II. The low TLV requires high sensitivity and stability in order to detect small amounts of Otto Fuel II on a continuous basis. Third, since Otto Fuel vapours tend not to spread rapidly, numerous detectors should be available to be positioned in likely spots of contamination. Thus, a relatively low cost is necessary to enable more of the detectors to be available. Fourth, the detector must be reliable and easy to operate since untrained individuals would use the monitor.

One known device operates on the principle that Otto Fuel II produces oxides of nitrogen when it decomposes and that the oxides react with a component in a detector tube to produce a colour change. This device does not produce an accurate reading of concentration, cannot monitor concentrations continuously, has a very slow response time, can only be used for short periods of time and has a relatively high average error. Thus, this device is obviously unsatisfactory on the basis of the criteria set forth above.

Other devices employ gas chromatography as the detecting method. While such methods have been found to be extremely sensitive, they are complex instruments to handle and, thus, use by untrained individuals is impossible. Further, these devices are rather expensive, require substantial maintenance, frequent calibration, and do not monitor on a continuous basis. Thus, while well suited for a laboratory environment, they are not practical for continuous monitoring and extensive in-field use.

Still others devices employ a Fourier Transform Infrared Spectroscopic detecting process. Their primary advantages, apart from their relatively high sensitivity, are that they can analyze air samples directly and can positively identify Otto Fuel II. However, these devices are not suitable because of cost and lack of portability.

A further device, known as the Graseby PD2-F Otto Fuel Detector, employs a sensitive electron capture detector as a sensing device and contains a argon cartridge for preconcentrating the Otto Fuel II. The preconcentrator consists of a platinum filament coated with an absorbent resin. Air is sucked over the platinum wire for a period of two seconds. The wire is then heated to desorb the Otto Fuel which is then carried by argon gas to the electron capture detector. The complete cycle takes approximately $3\frac{1}{2}$ seconds and is repeated continuously when the detector is on. Tests have shown that the detector is highly sensitive to Otto Fuel II concentrations in the range of 0.01 to 1.0 ppm. The device is portable, easy to use, has a high response time and thus appears to be ideally suited for spot checking areas of suspected contamination.

For long term monitoring, however, the latter device possesses a number of serious flaws. Firstly, it is provided with an autozero function which zeroes the detector to background air. Thus, unless the detector can be flushed out with non-contaminated air, it will eventually ignore the background concentration of Otto Fuel II. Secondly, the device cannot be used for extended periods of time without the availability of argon gas to replenish a portable bottle. Thirdly, the device is prone to interference by chlorinated compounds such as Freon 113 or trichloroethane which are used frequently in cleanup operations. Accordingly, a positive reading does not always indicate the presence of Otto Fuel II. Fourth, and among still other drawbacks, the device is relatively expensive thus precluding it from general use.

SUMMARY OF THE INVENTION

The present invention seeks to provide a method and an apparatus for detecting the presence and concentrations of vapours in a gaseous fluid and more specifically to a method and an apparatus for detecting the presence and concentration of Otto Fuel II in ambient air. In addition, the present seeks to provide an detector which is compact, portable, easy to use, relatively inexpensive, sensitive, selective, reliable and capable of continuous use.

The present invention is based on the principle that the resonant frequency of piezoelectric crystal varies inversely with the mass of the crystal. If the mass of the crystal is increased, the resonant frequency will decrease and, conversely, if the mass is decreased, the resonant frequency will increase. Thus, if such a crystal is coated with a substance which is capable of reversibly absorbing a vapour to be detected, absorbtion and desorbtion of the vapour by the coating will alter the mass and therefore the resonant frequency of the crystal in proportion to the quantity or concentration of vapour absorbed or desorbed. Thus, by establishing the relationship between vapour concentration and crystal frequency and monitoring the frequency of oscillation of the crystal, it is possible to determine the concentration of the vapour in a gaseous fluid in which the crystal is immersed.

While, under ideal conditions, it is possible to detect the vapour to low concentrations, long term frequency drifts due to the crystal coating, crystal electronics, changes in relative humidity and interference from other compounds, the single crystal approach may not be viable in some instances from a practical point of view.

These difficulties can be overcome by the provision of a second coated crystal, with similar response characteristics as the first, which is subjected to the same conditions as the first crystal except that it is isolated from the vapour by a vapour scavenging trap. The difference in frequency of the two crystals is thus a function of the vapour concentration and independent of humidity changes and background concentrations of solvents.

In order to remove long term drifts in crystal frequency, caused for example by thermal effects on crystal electronics and coatings, the crystal electronics are periodically re-zeroed by passing a gaseous fluid sample through a second scavenging trap to remove the vapour from the sample before the sample is passed over the two crystals.

In accordance with one aspect of the invention, there is provided a method of determining the concentration of a vapour in a gaseous fluid, comprising the steps of passing a sample of the fluid through a channel having therein a crystal oscillator coated with a substance which absorbs the vapour, monitoring the deviation of the frequency of the oscillator from a base-line frequency representative of a fluid sample having a zero concentration of the vapour and converting the frequency deviation, if any, to a numerical value indicative of the concentration of the vapour in the fluid.

In accordance with another aspect of the invention, there is provided a device for detecting the concentration of a vapour in a gaseous fluid, the device comprising a fluid manifold having an inlet passage for admitting fluid into the manifold and an outlet passage for discharging fluid from the manifold; a first fluid channel having a fluid inlet end in fluid communication with the fluid inlet passage and an outlet end in fluid communication with the manifold outlet passage, the channel having filter means therein for removing the vapour from fluid flowing through the channel; a second fluid channel having a fluid inlet end in fluid communication with the fluid inlet passage and an outlet end in fluid communication with the manifold outlet passage; a reference crystal oscillator adapted to oscillate at a predetermined base-line frequency in a vapour free environment disposed in the reference channel, the crystal being coated with a substance capable of reversibly absorbing the vapour and being operable to produce a first signal at a frequency representative of the concentration of vapour in the fluid passing through the reference channel; a measuring crystal oscillator adapted to oscillate at substantially the same predetermined base-line frequency disposed in the measuring channel, the measuring crystal being coated with a substance capable of reversible absorbing the vapour and being operable to produce a second signal at a frequency representative of the concentration of vapour in the fluid passing through the reference channel; and means responsive to the difference between the frequency of the first and second oscillators for producing a third signal representative of the concentration of vapour in the fluid flowing through the second channel and displaying the value of the concentration on a display.

BRIEF DESCRIPTION OF THE DRAWINGS

These and other features of the invention will become more apparent from the following description in which reference is made to the appended drawings, wherein.

DESCRIPTION OF A PREFERRED EMBODIMENT

The invention will now be described with reference to a method and an apparatus specifically adapted for detecting Otto Fuel II. However, it is to be understood at the outset, as explained more fully later, that the same concept can be used to detect the presence and concentration of other vapours or of simultaneously detecting the presence and concentrations of more than one vapour in a gaseous fluid. The ability to do so depends only upon the availability of suitable substances for coating the crystals.

Figure 1:
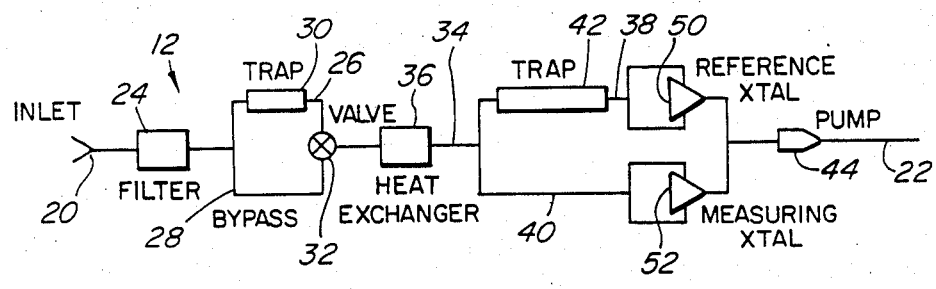
FIG. 1 is a diagrammatic illustration of the gaseous fluid flow path through a detector constructed in accordance with the present invention.
Figure 3:
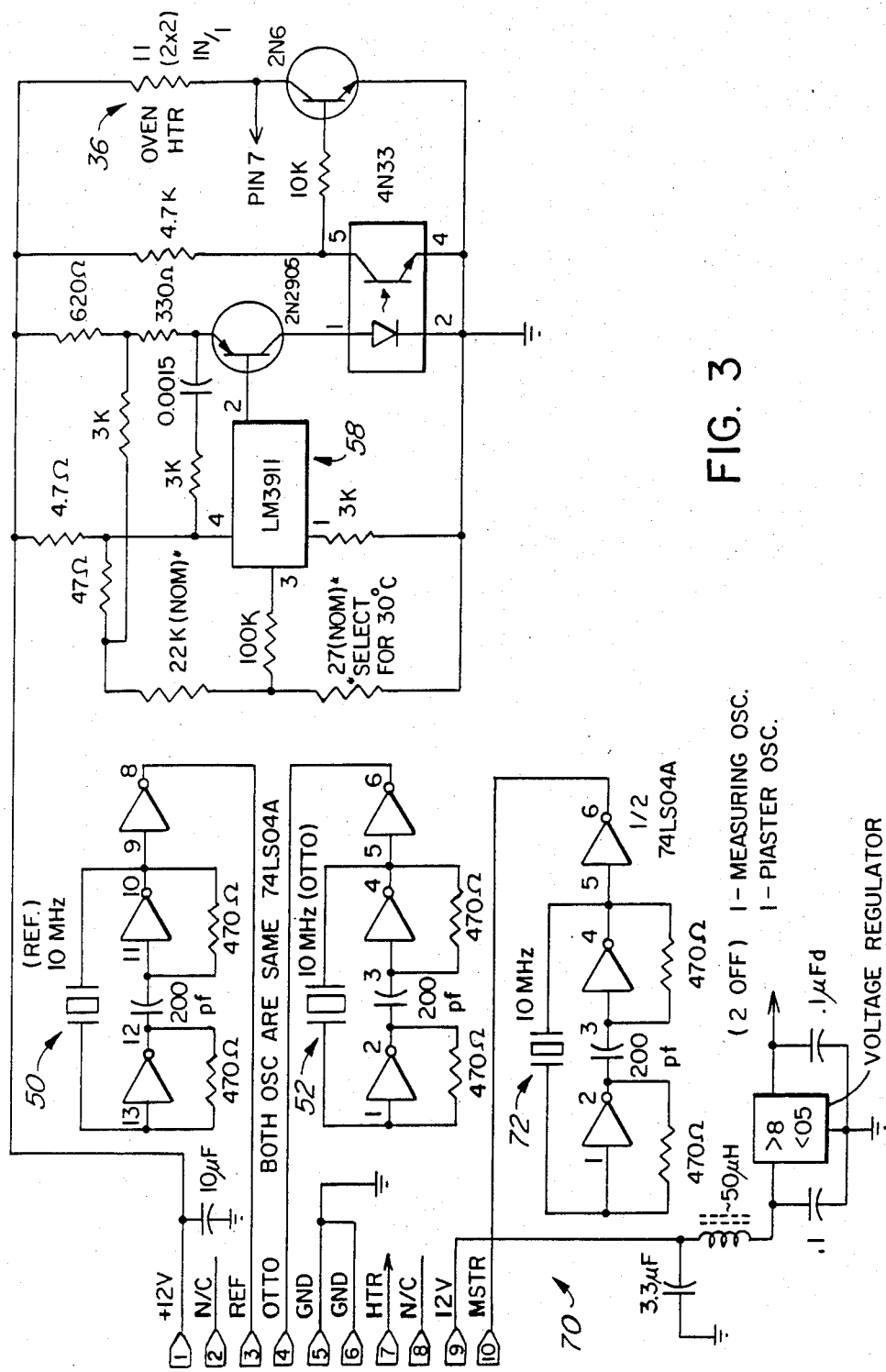
FIG. 3 is a circuit diagram of the detector head which includes reference and measuring oscillators, a master oscillator, a thermostat and heater circuitry.
Figure 4:
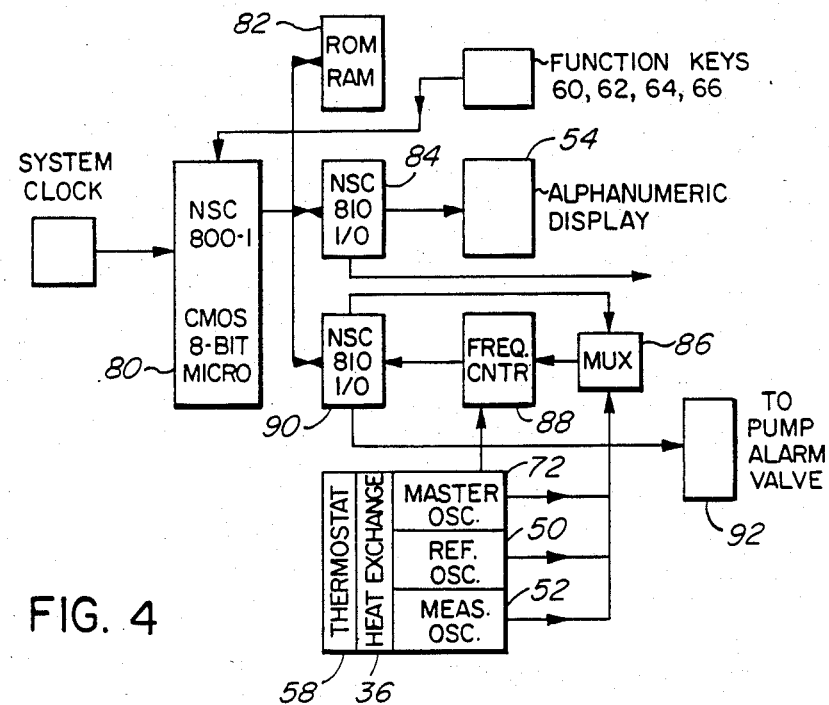
FIG. 4 is a block diagram illustrating the major components of an electrical circuit for monitoring the output of the reference and measuring crystal oscillators.
Figure 6:
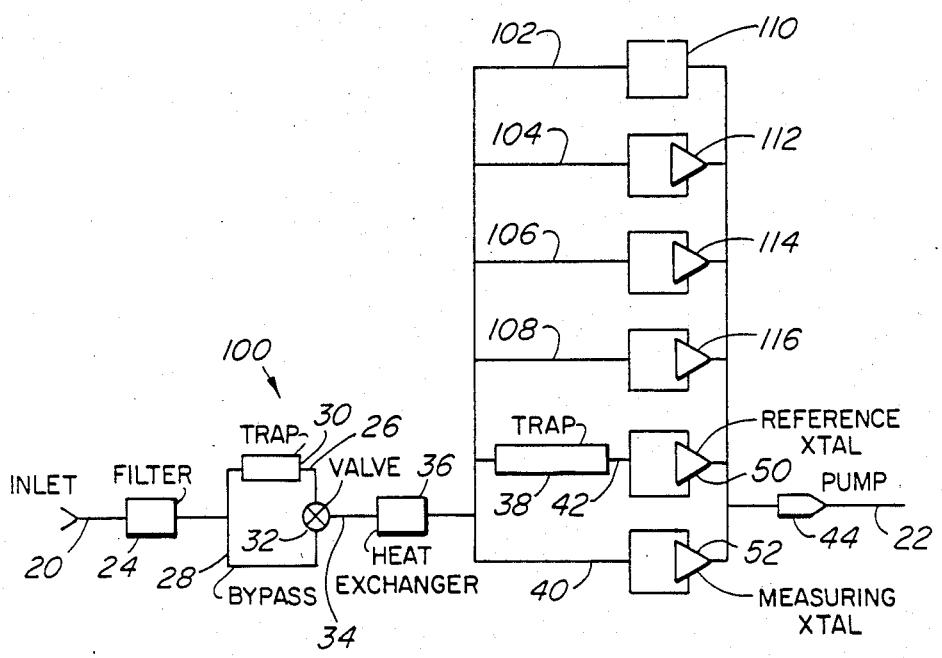
FIG. 6 is a view similar to FIG. 1 but illustrating a further embodiment of the present invention in which the device is adapted to detect the presence and concentration of other contaminants in ambient air.
Figure 5A:
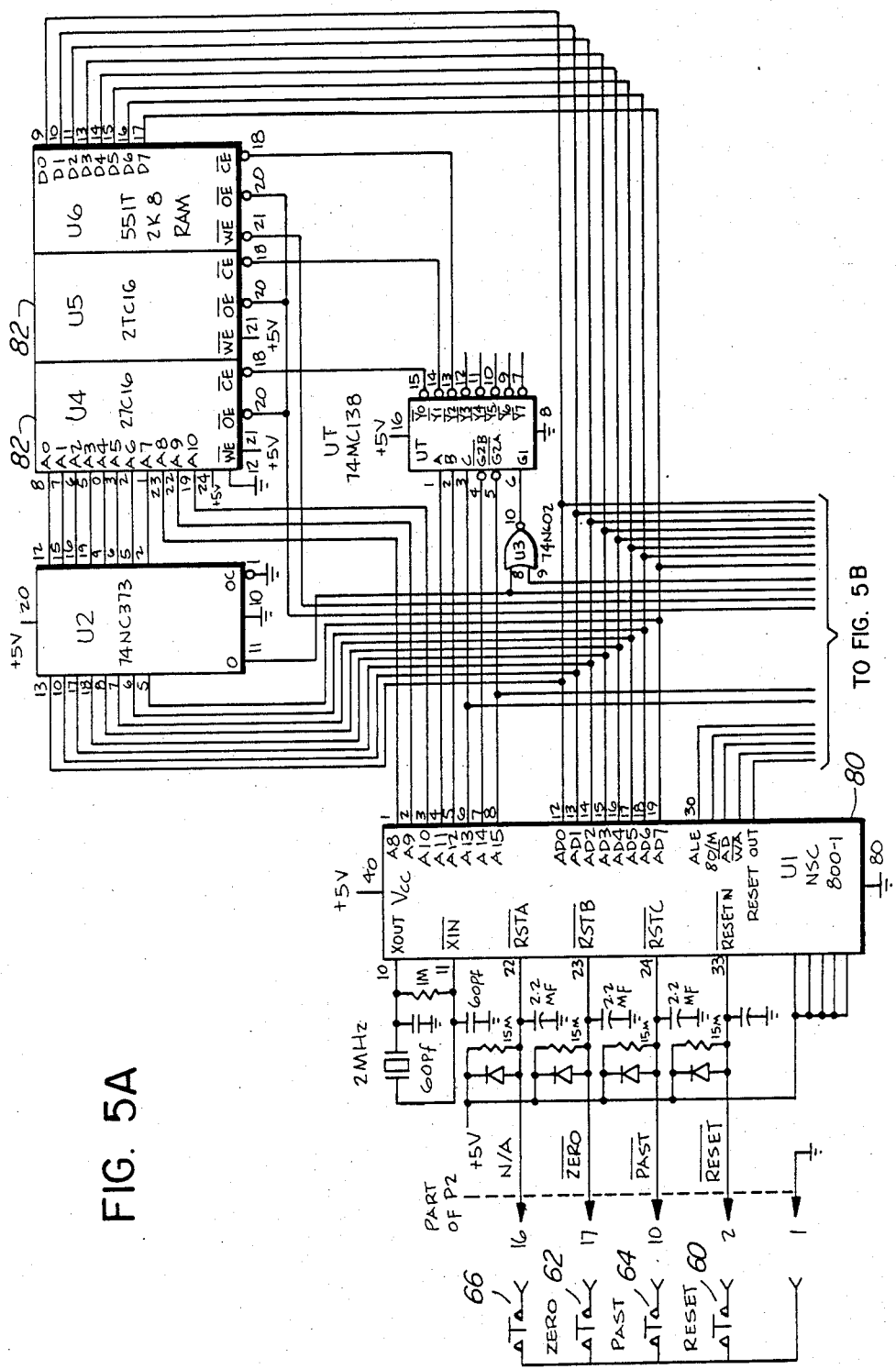
FIGS. 5A and 5B is a detailed circuit diagram of the of the circuit of FIG. 4.
Figure 5B:
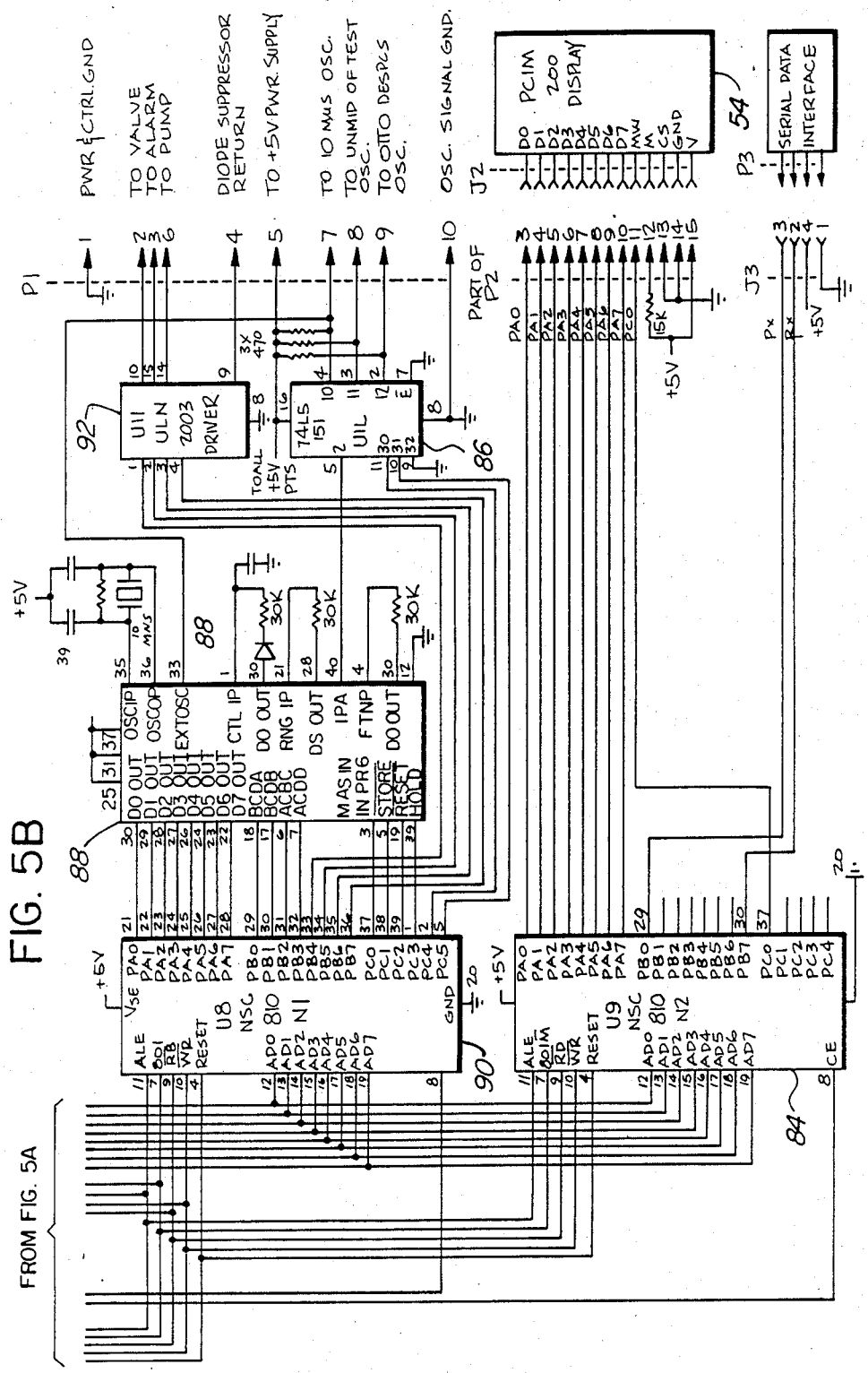

The Otto Fuel II concentration detector of the present invention, generally designated by reference numeral 10, includes a mechanical unit 12, diagrammatically illustrated in FIG. 1, and electronic monitoring circuitry 14, illustrated in block diagram form in FIG. 4 and schematically in FIGS. 3 and 5. The mechanical unit will be described first.

With reference to FIG. 1, there is diagrammatically illustrated a sample gaseous fluid flow path through a device for detecting the concentration of Otto Fuel II in ambient air. The device is comprised of a housing 16 having a manifold 18 including a gaseous fluid inlet passage 20 for admitting ambient air into the housing and an outlet passage 22 for discharging air from the housing. A suitable particulate filter 24 is disposed in the fluid inlet passage for removing particulate material from fluid entering the fluid inlet. The inlet passage splits into a fuel scavenging passage 26 and a bypass passage 28. The scavenging passage is provided with filter means 30, hereinafter referred to as a first scavenging trap, for removing Otto Fuel II from air flowing therethrough to enable re-zeroing of the monitoring electronics in a manner explained later. A computer controllable valve 32 is connected to the outlet end of each of passages 26 and 28 for selectively communicating one of the passages with a heat exchange passage 34 which contains heat exchanger means 36 for maintaining fluid flowing over the crystals within a predetermined temperature range. The fluid flow path then splits into a reference channel 38 and a measuring channel 40. A second filter means 42, hereinafter referred to a the second scavenging trap, is disposed in the reference channel for removing Otto Fuel II from fluid flowing therethrough. The two channels are joined at the inlet end of discharge passage 22 in which a two-speed vacuum pump 44 is disposed for continuously drawing gaseous fluid samples along the above described flow path.

A reference quartz piezoelectric crystal 50 is disposed in the reference channel while a measuring quartz piezoelectric crystal 52 is disposed in the measuring channel. Both crystals are coated with a substance, dicyanoallysilicone, which is capable of reversibly absorbing Otto Fuel II. Both crystals are arranged to oscillate at substantially the same resonant frequency of about 10 MHz in an Otto Fuel II free environment and are connected to electronic monitoring circuitry 14. The circuitry determines the frequency of both crystals, calculates the frequency difference between them and converts the difference into a numerical value expressed in parts per million (ppm) for display on an LCD display 54 on the front panel 56 of the instrument. The circuitry also controls the operation of the heat exchanger, the speed of operation of the pump and monitors a thermostat disposed in the heat exchange passage.

As previously mentioned, both crystals are coated with a uniform layer of dicyanoallysilicone. The amount of material applied to the crystals is most readily quantized on the basis of the frequency shift which results from the coating. It has been found that there is a limit to the amount of material which can be applied beyond which the crystals will not oscillate in the 10 MHz region. In particular, the maximum shift obtainable was about 110 kHz below the uncoated frequency. Crystals with that magnitude of frequency shift are very difficult to start oscillating and tend to operate very noisily. It has been found that a coating which results in a frequency shift of 50 to 60 kHz is optimum and that the sensitivity of the crystals does not increase significantly beyond this range. The two crystals should be made as uniform as possible, although the reference crystal should be made to have a slightly greater response (less than 5%) than that of the measuring crystal so that the presence of vapours other than Otto Fuel II will not produce a positive result.

The aforementioned traps 30 and 42 must be capable of removing Otto Fuel II from the air sample so as to provide a net frequency differential when Otto Fuel II is present in the air sample while not removing other vapours, including water vapour and isopropanol, to enable the two crystals to track together in the presence of such vapours. A simple arrangement which satisfies these requirements is a length of cellulose acetate butyrate tubing approximately 20 cm long and 6 mm O.D. When the first trap is bypassed by the valve, the second trap prevents Otto Fuel II from reaching the reference crystal and therefore a net frequency shift results from the output of the two crystals, assuming the presence of Otto Fuel II in the stream flowing through the measuring channel. The air sample is passed through the first trap at regular intervals so as to remove all Otto Fuel II from the stream passing in both channels so as to thereby zero the instrument.

The heat exchanger or preheater 36 is in the form of an electric resistance copper heater and serves to maintain the temperature of the air sample flowing through the reference and measuring channels at about 30° C. in order to minimize the effects of external temperature and thereby thermally stabilize both crystals and their coatings. The heater is controlled by the electronic circuit in response to the output of a thermostat 58 described later.

The pump is arranged to draw air samples at a rate of approximately 200 cm$^3$/min. for normal operation and at a rate of approximately 600 cm$^3$/min. for spot checking purposes. At the normal rate, the response time of the monitoring electronics is approximately 20 seconds for fairly high concentrations and slightly longer for lower concentrations.

Figure 2:
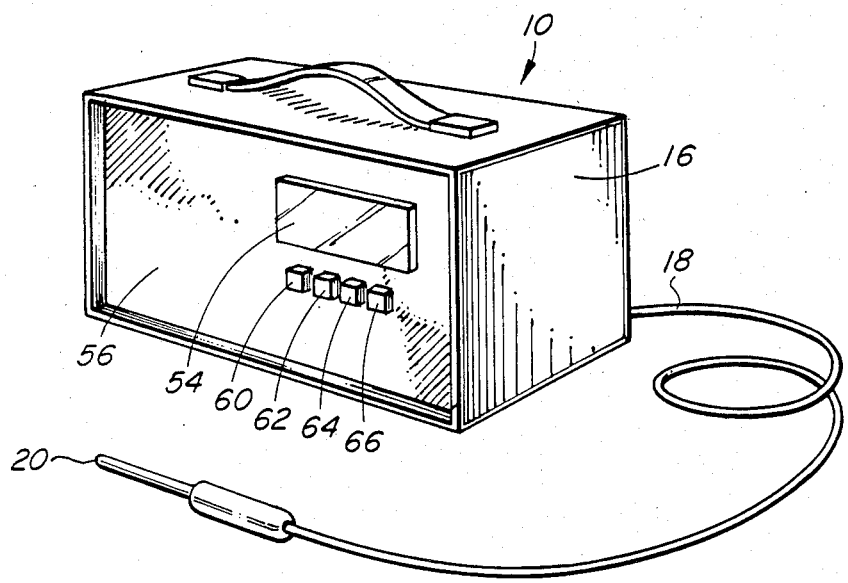
FIG. 2 is a perspective view of a device constructed in accordance with the present invention and illustrating the front panel thereof including an LCD display, a RE-SET button, an AUTO-ZERO button, a FAST button and an ON/OFF button.

In addition to the LCD display and, as best shown in FIG. 2, front panel 56 of the instrument is provided with a RE-SET button 60, an AUTO-ZERO button 62, a FAST button 64 and an ON/OFF switch 66. The instrument is also provided with an audio alarm 68 which is triggered by the monitoring electronics at Otto Fuel II concentrations of 0.5 ppm and higher.

FIG. 3 is a circuit diagram of the detector head electrical circuit 70 which includes the reference oscillator 50 measuring oscillator 52, a master oscillator 72, thermostat 58, based on an LM3911 temperature controller integrated circuit, and heater 36. The oscillators are low power Schottky integrated circuit invertors interconnected to provide an output to a multiplexer and frequency counter referenced below.

With reference to FIGS. 4 and 5, electronic monitoring circuitry 14 is generally comprised of a microprocessor 80, such as that available as Part No. NSC 800-1, which operates under the control of a program stored in two programmable read only memory (PROM) integrated circuits 82, available as Part No. 27C16. The microprocessor continuously monitors the status of instrument RE-SET key 60, AUTO-ZERO key 62 and FAST key 64 and operates in the manner explained below when one or more of these keys is depressed. Appendix A is a listing of a suitable machine language program stored in PROMs 82 for use by the microprocessor while Appendix B is a flow chart for that program.

The microprocessor outputs data, such as a numerical value of the Otto Fuel II concentration and system status to alpha-meric display 54 via a RAM-I/O-TIMER integrated circuit 84 available as Part No. NSC 810. The output of the reference and measuring oscillators, a master oscillator, the solid state thermostat and heater are fed to a multiplexer 86, available as Part No. 74LS151, and then to a frequency counter 88, available as Part No. ICM 7226B, which determines the frequency of the oscillators and the status of the thermostat, and heater and stores the data in a second RAM-I/O-TIMER integrated circuit 90 for ultimate use by the microprocessor. The latter RAM-I/O-TIMER integrated circuit also serves to transmit appropriate signals to the pump, alarm and valve via a peripheral-interface-adapter 92.

The device operates as follows. The instrument is plugged in to a 115 VAC outlet, and ON/OFF switch 66 and RE-SET key 60 are depressed. This initializes the microprocessor which activates heater 36 and pump 44. The program provides a period of 15 minutes to allow the crystal electronics to reach their operating temperature of about 30° C. before any measurements are taken.

Once the device has been warmed-up, AUTO-ZERO key 62 is depressed. This initiates the automatic zeroing routine in the program and the words "AUTO-ZERO-ING" appear on the display. The vacuum pump is activated to high speed pumping and valve 32 is switched to close bypass passage 28 and open first trap passage 26 to heat exchange passage 34. This purges the manifold and permits the monitoring electronics to be zeroed in Otto Fuel II free air. After 40 seconds, the pump speed is dropped to normal but the pump continues to draw air through the trap for an additional 50 seconds. The instrument then zeroes itself and the valve is switched to its normal position in which the first trap passage is closed and the bypass passage is opened. The microprocessor then displays the Otto Fuel II concentration on the display and updates it every 10 seconds. The instrument may then be used for routine monitoring of ambient air. The microprocessor activates the audio alarm when an Otto Fuel II concentration exceeding 0.5 ppm is detected.

FAST key 64 is depressed when it is desired to conduct a rapid spot check. This initiates the fast pumping cycle in order to decrease the response time of the instrument. During the first 20 seconds of this cycle, the instrument re-zeroes itself and the words FAST-ZEROING appear on the display. After 20 seconds, the display is reactivated and the instrument is ready for use. After about three minutes in the spot checking mode, the instrument automatically returns the pump to its normal pumping speed, re-zeroes itself, displaying the word ZEROING on the display while doing so, and thereafter continues normal operation.

It will be seen that the above described meets the criteria set forth at the outset. The device is compact and portable, extremely easy to use, relatively inexpensive in that all important components are readily available off-the-shelf items, selective, sensitive and reliable.

As previously mentioned, the present invention can readily be extended to detect the presence and concentration of vapours or contaminants other than Otto Fuel II or to simultaneously detect the presence and concentration of two or more different vapours. The ability to do so depends upon the availability of appropriate crystal coatings. Table I below identifies such substances and the vapours which can be detected thereby.

TABLE I

| Substance | Vapour Detected |
| --- | --- |
| Apiezon H TM | Distillate, Freon 12 |
| Apiezon M TM | Distillate (one half as sensitive to distillate as Apiezon H TM) |
| Tricresylphosphate | Otto Fuel |
| Dicyanoallylsilicone | Otto Fuel |

A device developed to provide an indication of percentage explosive, known as "hot wire", can also be employed in the device discussed below for that purpose.

Thus, in accordance with a further embodiment of the present invention, there is provided a manifold 100 which is similar to that described with reference to FIGS. 1 to 5 except that it is provided with four additional measuring channels 102, 104, 106 and 108. Channel 102 is provided with a hot wire 110, channel 104 with a crystal 112 coated with Apiezon H, channel 106 with a crystal 114 coated with Apiezon M and channel 108 with a crystal 116 coated with Tricresylphosphate.

As in the previous embodiment, the pump is caused to continuously pump air through the manifold with the flow being divided equally into each of the six channels. Each crystal responds characteristically to the flow depending on the contaminants in the air stream and its respective coating material. The relationship of the six outputs is used as the basis of determining the type or types of contaminant present in the sample, as explained hereinbelow.

As in the previous embodiment, the crystals are connected to monitoring electronics which include a microprocessor. The microprocessor reads and compares the output of each of the five measuring crystals and the hot wire and interprets the results as follows:

1. A positive output, indicating an explosive contaminant, from the hot wire indicates the presence of distillate fuel, Freon 12 or Otto Fuel II;
2. If the frequency shift of the Apiezon H crystal is twice as much as that of the Apiezon M crystal and the Tricresylphosphate crystal is inactive, the contaminant is Distillate and the display will show its concentration in ppm;
3. If the frequency shift of the Apiezon M crystal is low and not one half that of the Apiezon H crystal, the contaminant is Freon 12 and its concentration in ppm will be displayed;
4. If there is no frequency shift in the Apiezon crystals but there are shifts in the Tricresylphosphate and Dicyanoallylsilicone crystals, the contaminant is Otto Fuel II and the display will show its concentration in ppm.

It will be understood that, while the use of a microprocessor is deemed to be the best mode of putting the present invention into practice, a microprocessor is not essential in order to successfully practice the invention. For example, both the valve and the pump can readily be controlled manually and a thermostat can be made to control the heater directly in manners which are well known to those skilled in this field. The output of the oscillators could be applied to appropriate comparators which would determine the frequency and actuate a display and/or alarm. It will be understood that various other modifications and alterations may be made to the above described invention without departing from the spirit of the appended claims.

APPENDIX A - COMPUTER PROGRAM

```
;
;OTTO7.ASM
;
;
;PROM VERSION START AT 0000H , RAM AT 1000H
;
;A PROGRAMME FOR MEASURING GAS ABSORPTION ON
;XTALS COATED WITH SELECTIVE MATERIALS FOR
;MONITORING OTTO FUEL.
;
```

```
                ;
                ;
                ;
                ;
                ;
                ;
                ;
                ;
                ;
                ;
                ;
                ;          EQUATES FOR OTTO FUEL MONITOR
                ;
0032 =          MAXPPM:  EQU     32H       ;0.5PPM ALARM LEVEL
0040 =          PUMP:    EQU     40H       ;BIT FOR FAST PUMPING
0010 =          VALVE:   EQU     10H       ;BIT FOR AUTO-ZERO VALVE
0020 =          SONLRT:  EQU     20H       ;ALARM BIT FOR PORT 0C1H
00F0 =          FMODEB:  EQU     0F0H      ;BIT 0-3 IN AND 4-7 OUT.
00C1 =          FDATAB:  EQU     0C1H      ;ALARM AND PERF. OUTPUTS
00C5 =          FDRRB:   EQU     0C5H      ;DIR CTRL REGISTER PORT B
00C0 =          FDATAA:  EQU     0C0H      ;FREQ PORT A
00C4 =          FDRRA:   EQU     0C4H      ;DATA DIRECTION REGISTER A
0000 =          FMODEA:  EQU     00        ;MODE WORD 0=IN, 1=OUT BIT ASSIGNED
0020 =          DDATAA:  EQU     20H       ;DISPLAY PORT A
0024 =          DDRRA:   EQU     24H       ;DATA DIR.REG. A
0022 =          DDATAC   EQU     22H       ;DISPLAY PORT C STROBE
0026 =          DDRRC    EQU     26H       ;DIR REG FOR C
00FF =          DMODEA:  EQU     0FFH      ;ALL OUTPUTS
003C =          FMODEC:  EQU     3CH       ;BITS 0,1=IN  2-5=OUT
0004 =          REF:     EQU     04H       ;READ BIT FOR REF OSC
0014 =          OTTO:    EQU     14H       ;READ OTTO OSC
0024 =          HUMID:   EQU     24H       ;READ HUMID OSC
0000 =          RESET:   EQU     0         ;RESET 7226B,PORT C ONLY
0009 =          INTVL:   EQU     9         ;INTERVAL OF SAMPLING ç30 SEC
1200 =          BUF:     EQU     1200H     ;FREQ MEASURE BUFFER START
00ED =          NSCSTAT:          EQU     0EDH      ;NSC800 STATUS PORT
00EC =          NSCDATA:          EQU     0ECH      ;DATA PORT
1021 =          PUTC:    EQU     1021H     ;OUT CHR ROUTINE
00BB =          INTCR:   EQU     0BBH      ;INTERRPT CTRL REG.
101B =          RSTA:    EQU     101BH     ;JMP ADR FOR RSTA
1015 =          RSTB:    EQU     1015H     ;JMP RSTB
100F =          RSTC:    EQU     100FH     ;JMP RSTC
1203 =          RMSD:    EQU     BUF+3H    ;REF MSD FREQ BCD CURRENT
120D =          OMSD:    EQU     BUF+0DH   ;OTTO MSD FREQ BCD CURRENT
1217 =          HMSD:    EQU     BUF+17H   ;HUMID BCD CURRENT
121F =          ODELT:   EQU     BUF+1FH   ;OTTO DELTA FROM INITAL
1227 =          HDELT:   EQU     BUF+27H   ;HUMIDITY DELTA
1240 =          REFI:    EQU     BUF+40H   ;INITAL REF BCD
1248 =          OTTOI:   EQU     BUF+48H   ;INITAL OTTO BCD
1250 =          HUMI:    EQU     BUF+50H   ;INITAL HUMIDITY BCD
122F =          DMSD:    EQU     BUF+2FH   ;DIFFERENCE BCD
1237 =          PPMSD:   EQU     BUF+37H   ;CONC READOUT BCD
123D =          LEND:    EQU     BUF+3DH   ;END OF LINE
1258 =          RBIN:    EQU     BUF+58H   ;REF BIN CURRENT
125A =          OBIN:    EQU     BUF+5AH   ;OTTO BIN CURRENT
125C =          HBIN:    EQU     BUF+5CH   ;HUMID BIN CURRENT
125E =          RBINI:   EQU     BUF+5EH   ;REF BIN INITAL
1260 =          OBINI:   EQU     BUF+60H   ;OTTO BIN INITAL
1262 =          HBINI:   EQU     BUF+62H   ;HUMIDITY BIN INITAL
1264 =          TEMP:    EQU     BUF+64H   ;TEMP STORE DIV
1266 =          BNUM:    EQU     BUF+66H   ;BIN NUM STORE
1268 =          ODBIN:   EQU     BUF+68H   ;OTTO DELTA BIN
126A =          HDBIN:   EQU     BUF+6AH   ;HUMIDITY DELTA BIIN
```

```
126C =              DFBIN:  EQU     BUF+6CH  ;DIFFERENCE BIN
126E =              SAVE:   EQU     BUF+6EH  ;TEMP STORE
1270 =              SAVE1:  EQU     BUF+70H  ;TEMP STORE
1272 =              LSTDF:  EQU     BUF+72H  ;LAST DIIFFERENCE
1274 =              INITAL: EQU     BUF+74H  ;INITAL READINGS FOR SUBR
1276 =              CURR:   EQU     BUF+76H
127A =              AZERO:  EQU     BUF+7AH  ;AUTO ZERO COUNTER
127C =              FSCNT:  EQU     BUF+7CH  ;FAST PUMP COUNTER
1278 =              PIAWRD: EQU     BUF+78H  ;CONTL WORD FOR VALV,ALRM,PUMP
127E =              PPMDSP: EQU     BUF+7EH  ;TEMP STORE FOR DISPLAY STRING
000A =              LPPM:   EQU     10       ;DIVISOR FOR CONC <1PPM
0006 =              HPPM:   EQU     6        ;DIVISOR FOR CONC >1PPM
0026 =              INTR:   EQU     38       ;INTERCEPT FOR HI PPM SLOPE
0062 =              TLPPM:  EQU     98       ;TEN X LPPM FOR 0.1PPM RESOLUTION
                    ;FREQ COUNTER IS 10SEC SAMPLE,ALLOWS FOR 0.1PPM RES.
                    ;
                    ;PORT B=PORT A+1 AND PORT C=PORT A+2
                    ;THIS APPLIES TO DATA AND DIRECTION REGISTER
                    ;
                    ;
0000                        ORG     0000H    ;BEGIN RESTART VECTORS
0000 C38000                 JMP     0080H    ;RESTART AND RESET
                    ;
002C                        ORG     02CH
002C C37404                 JMP     0474H    ;FAST PUMPING VECTOR
                    ;
0034                        ORG     034H
0034 C3CC04                 JMP     04CCH    ;AUTO ZERO VECTOR
                    ;
003C                        ORG     03CH
003C C38000                 JMP     0080H    ;NOT IMPLEMENTED
                    ;
                    ;
0080                        ORG     0080H    ;START OF FREE MEM OF NSC800
                    ;
0080 3E3C           INIT:   MVI     A,FMODEC         ;SET UP FREQ PL..;
0082 D3C6                   OUT     FDRRA+2  ;OUTPUT TO PORT C
0084 3EF0                   MVI     A,FMODEB         ;DATA DIR FOR PORT B
0086 D3C5                   OUT     FDRRB    ;SET PORT B
0088 31FF17                 LXI     SP,17FFH         ;OWN SPACK
008B 3EFF                   MVI     A,DMODEA         ;SET UP DISPLAY PORT
008D D324                   OUT     DDRRA    ;OP TO PORT A
008F D326                   OUT     DDRRC    ;SET UP C TO ALL OUT ALSO
0091 3E0E                   MVI     A,0EH    ;MASK FOR RSTA,B,C
0093 D3B8                   OUT     INTCR    ;SET MASK
0095 FB                     EI               ;ENABLE NMI
0096 211C10                 LXI     H,RSTA+1         ;ADR OF RSTA JMP VECTOR
0099 3630                   MVI     M,30H    ;PUT IN LO BYTE , UNDEFINED
009B 23                     INX     H
009C 3610                   MVI     M,10H    ;AND HI BYTE
009E 211610                 LXI     H,RSTB+1         ;AUTO/ZERO FUNC VECTOR
00A1 3678                   MVI     M,78H
00A3 23                     INX     H
00A4 3614                   MVI     M,14H
00A6 211010                 LXI     H,RSTC+1         ;FAST PUMP VECTOR
00A9 3623                   MVI     M,23H
00AB 23                     INX     H
00AC 3614                   MVI     M,14H
00AE 214304                 LXI     H,INTDS  ;PNT TO STRING FOR DISPLAY INIT
00B1 CD2404                 CALL    DSPOUT   ;OUTPUT THE STRING
                    ;
                    ;ALL OTHER PORTS ARE INITALIZED AS INPUTS
```

```
0084 0E40      START:   MVI    C,40H      ;FILL 40H LOC W/SPACES-40H
0086 210012             LXI    H,BUF      ;PNT TO START OF BUFFER
0089 36F0      START1:  MVI    M,0F0H
008B 23                 INX    H
008C 0D                 DCR    C
008D C28900             JNZ    START1     ;FILL 40
00C0 210000             LXI    H,0000H    ;INITALIZE DIF BIN.
00C3 226C12             SHLD   DFBIN
00C6 227212             SHLD   LSTDF      ;INIT LAST DIFFER
00C9 227612             SHLD   PIAWRD     ;SET ALL PERF OFF
00CC CDC203             CALL   ALARM      ;SHUT OFF ALL PERF DEVICES
00CF CD2301    START2:  CALL   START6     ;DO INITAL READINGS
00D2 217A12    START3:  LXI    H,AZERO    ;PNT TO AUTOZ CNTR
00D5 3696               MVI    M,96H      ;150Q X 10 SEC=30MIN WAIT
00D7 0602      START4:  MVI    B,02       ;12 SEC LOOP
00D9 CDE900             CALL   START5     ;MAIN COUNTER/DISPLAY LOOP
00DC 217A12             LXI    H,AZERO    ;DO THIS FOR 30 MIN
00DF 35                 DCR    M          ;LOOP
00E0 C2D700             JNZ    START4
00E3 CDCC04             CALL   AUTOZ      ;DO A REZERO
00E6 C3D200             JMP    START3     ;CONTINUE READINGS
00E9 210012    START5:  LXI    H,BUF      ;PNT TO BUF START
00EC 0E04               MVI    C,REF      ;MUX CNTRL WORD FOR REF OSC
00EE CD3601             CALL   RDOSC      ;READ THE FREQ OF OSCILLATOR
00F1 CD5601             CALL   SPACE      ;INSERT 2 SPACES
00F4 0E14               MVI    C,OTTO     ;MUX FOR OTTO OSC
00F6 CD3601             CALL   RDOSC
00F9 CD5601             CALL   SPACE
00FC 0E24               MVI    C,HUMID    ;MUX WORD FOR HUMID OSC
00FE CD3601             CALL   RDOSC
0101 CD5601             CALL   SPACE
0104 213D12             LXI    H,LEND     ;PNT TO END OF LINE
0107 36DA               MVI    M,0DAH     ; "LF"-30H
0109 23                 INX    H
010A 36DD               MVI    M,0DDH     ;"CR"-30H
010C 23                 INX    H
010D 36FF               MVI    M,0FFH     ;INSERT END OF MSG CHR
010F 05                 DCR    B          ;BUMP INTERVAL COUNTER
0110 C2E900             JNZ    START5     ;DO IT FOR THE FULL TIME
0113 CD1D03             CALL   DELTA      ;CAL FREQ CHANGES
0116 CD2403             CALL   VALID      ;TEST READINGS &CNVT IF OK
0119 CDC203             CALL   ALARM      ;SOUND ALARM IF PPM ABOVE SAFE LEVEL
011C CDED03             CALL   DISPLAY    ;PUT UP PPM READINGS
011F CD6401             CALL   PRINT      ;PRINT THE READINGS
0122 C9                 RET 0123 214012    START6:  LXI    H,REFI     ;POINT TO INITAL REF
0126 0E04               MVI    C,REF      ;MUX WRD FOR REF
0128 CD3601             CALL   RDOSC      ;READ OSC
012B 0E14               MVI    C,OTTO     ;WRD FOR OTTO
012D CD3601             CALL   RDOSC
0130 0E24               MVI    C,HUMID
0132 CD3601             CALL   RDOSC
0135 C9                 RET 0136 3E00      RDOSC:   MVI    A,RESET    ;RESET THE 7226B COUNTER
0138 D3C2               OUT    FDATAA+2   ;OP TO PORT C
013A 79                 MOV    A,C        ;LOAD WHICH COUNTER
013B D3C2               OUT    FDATAA+2              ;SWITCH THE MUX
013D DBC2      STAT:    IN     FDATAA+2              ;GET 7226B STATUS
013F E602               ANI    2          ;IS IT STORE
```

```
0141 C23D01                JNZ     STAT        ;WAIT FOR STORE
0144 0E80                  MVI     C,80H       ;POINT TO DIGIT 7
0146 DBC0      DIGIT:  IN          FDATAA      ;GET DIGIT FLAG
0148 A1                    ANA     C           ;IS IT CORRECT DIGIT
0149 CA4601               JZ       DIGIT       ;WAIT FOR IT
014C CD5D01               CALL     GETBCD      ;OK GET BCD DATA
014F 79                    MOV     A,C         ;GET BACK DIGIT POINTER
0150 0F                    RRC                 ;NEXT LSD
0151 4F                    MOV     C,A         ;SAVE IT
0152 D24601               JNC      DIGIT       ;DO ALL DIGITS
0155 C9                    RET
0156 3EF0      SPACE:  MVI         A,0FOH      ;SPACE-30H
0158 77                    MOV     M,A
0159 23                    INX     H
015A 77                    MOV     M,A
015B 23                    INX     H
015C C9                    RET
                ;
                ;
015D DBC1      GETBCD: IN          FDATAA+1    ;GET PORT B BCD DATA
015F E60F                  ANI     0FH         ;MASK OFF 4LSB'S
0161 77                    MOV     M,A         ;PUT IN BUFFER
0162 23                    INX     H
0163 C9                    RET
                ;
                ;
0164 C9        PRINT:  RET                     ;DUMMY RETURN AS PRINT DISABLED
                                               ;FOR PROM VERSION
0165 210012               LXI      H,BUF       ;POINT TO START OF READINGS
0168 7E        PRINT1: MOV         A,M         ;GET DATA
0169 FEFF                  CPI     0FFH        ;IS IT END OF MSG?
016B C8                    RZ                  ;ALL DONE?
016C C630                  ADI     30H         ;ADD ASCII OFFSET
016E CD2110               CALL     PUTC        ;OUTPUT A CHR
0171 23                    INX     H           ;NXT DIGIT
0172 C36801               JMP      PRINT1      ;KEEP GOING
                ;
                ;
                ;
                ;
0175 11001A    WAIT:   LXI         D,1A00H     ;50 MS DELAY
0178 1D        WAIT1:  DCR         E
0179 C27801               JNZ      WAIT1
017C 15                    DCR     D
017D C27801               JNZ      WAIT1
0180 C9                    RET
                ;
                ;CNVRT BCD TO BINARY , ENTER A= # OF DIGITS
                ;DE=PNTR TO MSD OF BCD, EXIT DE=BIN NUMBER
                ;
0181 210000    CNVRT:  LXI         H,0000      ;CONVERT BCD TO BIN
0184 3E05                  MVI     A,05        ;#DIGITS
0186 E5        CNVRT1: PUSH        H
0187 C1                    POP     B           ;HL TO BC
0188 29                    DAD     H           ;X2
0189 29                    DAD     H           ;X4
018A 09                    DAD     B           ;X5
018B 29                    DAD     H           ;X10
018C EB                    XCHG                ;DE PNTR TO DEC DIG
018D 4E                    MOV     C,M         ;GET LSD
018E EB                    XCHG                ;GET BACK PARTIAL SUBTRN
018F 0600                  MVI     B,0
```

```
0191 09              DAD   B        ;ADD BYTE
0192 13              INX   D        ;POINT TO NXT DIGIT
0193 3D              DCR   A        ;DEC DIGIT CNTR
0194 C28601          JNZ   CNVRT1   ;DO TILL 4 DIGITS
0197 EB              XCHG           ;SAVE BIN POINTERS
0198 C9              RET
                ;
                ;
                ;
                ;SUB80: A MULTIPLE BYTE SUBTRACT. ENTER C=# OF BYTES
                ;DE=PNTR TO MINUEND, HL=PNTR TO SUBTRAHEND, EXIT
                ;HL=PNT TO RESULT  A=ERROR FLAG,IF A=FF THEN ERROR
                ;ALL PNTRS ARE TO LSBYTE.
                ;
                ;
0199 AF       SUB80: XRA   A        ;CLR ALL
019A 1A       SBT1:  LDAX  D        ;LOAD GTTO
019B 9E              SBB   M        ;SUB HUMID
019C 77              MOV   M,A         ;PUT PARTIAL ANS IN HUMID
019D 23              INX   H
019E 13              INX   D        ;NXT BYTES
019F 0D              DCR   C        ;DO TILL 2BYTES
01A0 C29A01          JNZ   SBT1     ;KEEP GOING
01A3 D0              RNC            ;IF NO CARRY OK
                ;IF AN ERROR DO A RESTART
                ;
01A4 31FF1F   ERROR: LXI   SP,1FFFH               ;THROW OUT RETS
01A7 216812          LXI   H,ODBIN  ;PNT TO CURRENT READINGS
01AA 0E0B            MVI   C,0BH    ;THERE ARE 5 DBYTS
01AC 3600     ERROR1: MVI  M,0      ;ZERO THEM
01AE 23              INX   H
01AF 0D              DCR   C
01B0 C2AC01          JNZ   ERROR1   ;ALL
01B3 3EF0            MVI   A,0F0H   ;CLEAR THE DISPLAY
01B5 D320            OUT   DDATAA   ;AS A ERROR FLAG
01B7 C3D200          JMP   START3   ;DO A REST
                ;
                ;
                ;
01BA 215C12   UCNVRT: LXI  H,HBIN   ;DIF BIN
01BD 5E              MOV   E,M      ;GET LOBYTE
01BE 23              INX   H        ;NXT BYTE
01BF 56              MOV   D,M
01C0 212F12          LXI   H,DMSD           ;PNT TO DIF MSD
                ;
                ;
                ;BINDEC BINARY TO DECIMAL CONVERSION , ENTER
                ;DE=NUMBER TO BE CONVERTED ,HL STORE FOR DEC NUMBER,
                ;PNTRS ARE FOR MSDIGIT.
                ;
01C3 F5       BINDEC: PUSH PSW
01C4 C5              PUSH  B
01C5 D5              PUSH  D
01C6 E5              PUSH  H
01C7 EB              XCHG
01C8 01F0D8          LXI   B,0D8F0H         ;10,000 IN 2 COMP
01CB CDE701          CALL  TOCMP
01CE 0118FC          LXI   B,0FC18H         ;1000 2 COMP
01D1 CDE701          CALL  TOCMP
01D4 019CFF          LXI   B,0FF9CH         ;100
01D7 CDE701          CALL  TOCMP
01DA 01F6FF          LXI   B,0FFF6H         ;10
```

```
01DD CDE701          CALL    TOCMP
01E0 7D              MOV     A,L
01E1 12              STAX    D
01E2 E1              POP     H
01E3 D1              POP     D
01E4 C1              POP     B
01E5 F1              POP     PSW
01E6 C9              RET
                ;
                ;
                ;
                ;
01E7 AF      TOCMP:  XRA     A          ;CLR ALL
01E8 D5              PUSH    D          ;SAVE
01E9 5D      TOCM1:  MOV     E,L        ;MAKE DE=HL
01EA 54              MOV     D,H
01EB 3C              INR     A          ;A ONE
01EC 09              DAD     B          ;ADD CONSTANT
01ED DAE901          JC      TOCM1      ;IF CARRY DO AGAIN
01F0 3D              DCR     A
01F1 6B              MOV     L,E
01F2 62              MOV     H,D
01F3 D1              POP     D
01F4 12              STAX    D
01F5 13              INX     D
01F6 C9              RET
                ;
                ;
                ;DIV80: 16X16 DIVIDE, ENTER DE=DIVIDEND,HL=DIVISOR,
                ;EXIT DE=RESULT,HL=REMAINDER.
                ;
01F7 226412  DIV80:  SHLD    TEMP       ;SAVE DIVIDEND IN TEMP
01FA 216612          LXI     H,BNUM     ;STORE
01FD 3611            MVI     M,11H      ;BIT COUNT
01FF 010000          LXI     B,0        ;INIT RESULT
0202 C5              PUSH    B          ;SAVE RESULT ON STACK
0203 7B      LOOP:   MOV     A,E        ;GET LO DIVISOR BYTE
0204 17              RAL
0205 5F              MOV     E,A        ;SHIFT DIVISOR LEFT ONE BIT
0206 7A              MOV     A,D
0207 17              RAL                ;RET DIVISOR TO DE
0208 57              MOV     D,A
0209 35              DCR     M          ;DEC BIT CNT
020A E1              POP     H          ;RESTORE TEMP RESULT
020B C8              RZ                 ;IF ZERO BIT,THEN DONE
020C 3E00            MVI     A,0        ;ADD IN
020E CE00            ACI     0          ;CARRY
0210 29              DAD     H          ;SHIFT TEMP RESULT LEFT 1 BIT
0211 44              MOV     B,H        ;COPY HL TO A & C
0212 85              ADD     L
0213 2A6412          LHLD    TEMP       ;GET ADR OF DIVIDEND
0216 95              SUB     L          ;SUBT FROM
0217 4F              MOV     C,A
0218 78              MOV     A,B
0219 9C              SBB     H          ;TEMPORY RESULT
021A 47              MOV     B,A
021B C5              PUSH    B          ;SAVE TEMP ON STACK
021C D22102          JNC     SKIP       ;NO BORROW ON SUBT
021F 09              DAD     B          ;ADD DIVIDEND BACK IN
0220 E3              XTHL               ;REPLACE TEMP RESULT ON STACK
0221 216612  SKIP:   LXI     H,BNUM     ;RESTORE HL
```

```
0224 3F                 CMC
0225 C30302             JMP     LOOP    ;REPEAT LOOP STEPS
                        ;
                        ;
                        ;CONVERT DIFFERENCE OF READINGS TO PPM OTTO FUEL.
                        ;
0228 216C12     PPM:    LXI     H,DFBIN ;DIFFER OF DELTA O AND H
022B 46                 MOV     B,M     ;SAVE LO BYTE
022C 23                 INX     H       ;DIF HI BYTE
022D 4E                 MOV     C,M
022E 216200             LXI     H,TLPPM ;HI BYTE OF DIVISOR
0231 7C                 MOV     A,H
0232 B9                 CMP     C
0233 DA4402             JC      GRT1    ;DIFF>LPPM HI BYTE SO DO IT
0236 7D                 MOV     A,L     ;LO BYTES NOW
0237 B8                 CMP     B
0238 DA4402             JC      GRT1    ;STILL >1
023B 58                 MOV     E,B     ;PUT DIFF IN DE
023C 51                 MOV     D,C
023D 210A00             LXI     H,LPPM  ;SO IT <1 SO DO THAT
0240 CD5B02             CALL    DIVCON  ;DO DIV AND CONVERT
0243 C9                 RET
                        ;
                        ;
                        ;ROUTINE TO SUBTRACT INTERCEPT FROM DIF READING BEFORE
                        ;CONVERSION TO PPM OTTO FUEL.
                        ;REQUIRED ONLY FOR CALC. OF GREATER THAN 1 PPM.
                        ;
0244 216C12     GRT1:   LXI     H,DFBIN ;GET DIF BIN
0247 112600             LXI     D,INTR  ;DE=HPPM INTERCEPT
024A AF                 XRA     A       ;CLEAR ALL FLAGS
024B 7E                 MOV     A,M     ;GET LOBYTE DIF BIN
024C 9B                 SBB     E       ;SUBT INTERCEPT
024D 77                 MOV     M,A     ;SAVE LOBYTE
024E 23                 INX     H       ;GET    HIBYTE
024F 7E                 MOV     A,M     ;HIBYTE FOR SUBT
0250 9A                 SBB     D       ;FIX UP BORROW
0251 57                 MOV     D,A     ;SAVE HI BYTE
0252 2B                 DCX     H       ;SET HBIN BSCK TO LOBYTE
0253 5E                 MOV     E,M     ;LO BYTE OF SUBT
0254 210600             LXI     H,HPPM  ;GET HPPM DIVISOR
0257 CD5B02             CALL    DIVCON  ;DIVIDE AND COV TO BCD
025A C9                 RET
                        ;
                        ;DIVIDE DELTA BY SLOPE FOR PPM DETERMINATION.
                        ;
025B CDF701     DIVCON:         CALL    DIV80   ;DO 16X16 DIVIDE
025E 213812             LXI     H,PPMSD+1       ;WHERE BCD NUM GOES, ALLOW FOR SIGN
0261 CDC301             CALL    BINDEC  ;CONVERT TO BCD
0264 C9                 RET
                        ;
                        ;DBCMP-DOUBLE BYTE COMPARE OF TWO MEMORY WORDS, ENTER WITH
                        ;HL POINTING TO FIRST AND DE TO THE SECOND. - EXIT WITH HL
                        ;POINTING TO THE LARGER NUMBER AND ACCM INDICATING IF HL
                        ;POINTER CHANGED, ACCM=0 NOCHANGE, FF IF CHANGED.
                        ;
0265 23         DBCMP:  INX     H       ;POINT TO HI BYTES
0266 13                 INX     D
0267 7E                 MOV     A,M     ;MOVE HI FIRST IN
0268 2B                 DCX     H       ;POINT TO LO FIRST
0269 4E                 MOV     C,M     ;MOVE LO FIRST IN
026A EB                 XCHG            ;HL POINTS TO LO SECOND
```

```
026B BE                 CMP     M           ;IS HI SECOND > LO FIRST
026C 2B                 DCX     H           ;POINT TO LO SECOND
026D D27302             JNC     SFLAG       ;GOTO SET FLAG & POINTERS
0270 3EFF       DBCMP1: MVI     A,0FFH      ;SET FLAG DE>HL
0272 C9                 RET
                ;
0273 C27E02     SFLAG:  JNZ     SFLAG1      ;SECOND>FIRST
0276 79                 MOV     A,C         ;SEC=FIR, INITAL LO TO A
0277 BE                 CMP     M           ;CURR LO
0278 D27E02             JNC     SFLAG1      ;INIT>CURR
027B C37002             JMP     DBCMP1      ;CURR>INITAL
027E 3E00       SFLAG1: MVI     A,0         ;HL>DE
0280 EB                 XCHG                ;PNT TO HL
0281 C9                 RET
                ;
                ;
                ;
                ;ROUTINE TO CONVERT ALL INITAL AND CURRENT READINGS TO BIN
                ;
0282 110312     INLBIN: LXI     D,RMSD      ;ALL BIN # ARE STORED IN SEQUENCE
0285 215812             LXI     H,RBIN      ;HL IS INX BY RDCNVT
0288 CDAA02             CALL    RDCNVT      ;CONVERT AND STORE
028B 110D12             LXI     D,OMSD
028E CDAA02             CALL    RDCNVT
0291 111712             LXI     D,HMSD
0294 CDAA02             CALL    RDCNVT
0297 114312             LXI     D,REFI+3
029A CDAA02             CALL    RDCNVT
029D 114B12             LXI     D,OTTOI+3                   ;PNT TO 3RDMSD
02A0 CDAA02             CALL    RDCNVT
02A3 115312             LXI     D,HUMI+3
02A6 CDAA02             CALL    RDCNVT
02A9 C9                 RET
                ;
                ;ENTER DE=PNTR TO MSD OF BCD, HL=PNTR BIN STORE
                ;
02AA E5         RDCNVT: PUSH    H           ;SAVE BIN STORE PNTR
02AB CD8101             CALL    CNVRT       ;DO CONVERSION
02AE E1                 POP     H           ;GET BACK PNTR
02AF 73                 MOV     M,E         ;PUT RESULTS IN MEM
02B0 23                 INX     H           ;NXT
02B1 72                 MOV     M,D
02B2 23                 INX     H           ;SET UP FOR NXT CNVRT
02B3 C9                 RET
                ;
                ;ROUTINE TO COMPARE INITAL AND CURRENT READINGS, DET'N
                ;SIGN AND CALCULATE DELTA FOR OTTO AND HUMIDITY FREQ'S.
                ;
02B4 2A6012     RDCMP:  LHLD    OBINI       ;USE COPIES OF READINGS
02B7 227412             SHLD    INITAL
02BA 2A5A12             LHLD    OBIN
02BD 227612             SHLD    CURR
02C0 217412             LXI     H,INITAL    ;PNT TO IT
02C3 117612             LXI     D,CURR
02C6 CD6502             CALL    DBCMP       ;2BYTE CMP
02C9 226E12             SHLD    SAVE        ;SAVE LARGER # PNTR
02CC 211F12             LXI     H,ODELT     ;PNT TO SIGN LOC. FOR OTTO
02CF CDF902             CALL    SGNDEL      ;DETRN SIGN AND CALUATE DELTA
02D2 EB                 XCHG                ;DE HAVE DIF OTTO
02D3 226812             SHLD    ODBIN       ;SAVE IT
02D6 2A6212             LHLD    HBINI       ;MAKE COPIES
02D9 227412             SHLD    INITAL
02DC 2A5C12             LHLD    HBIN
```

```
02DF 227612              SHLD    CURR
02E2 217412              LXI     H,INITAL          ;INITAL HUMID
02E5 117612              LXI     D,CURR    ;CURRENT HUMID
02E8 CD6502              CALL    DBCMP     ;COMPARE
02EB 226E12              SHLD    SAVE      ;SAVE DBCD PNTR
02EE 212712              LXI     H,HDELT   ;PNT TO SGN LOC HUMID
02F1 CDF902              CALL    SGNDEL    ;DET SGN AND CAL DELTA HUMIDITY
02F4 EB                  XCHG              ;DE HAVE DIF HUMID
02F5 226A12              SHLD    HDBIN     ;SAVE IT
02F8 C9                  RET
                ;
                ;INSTALL SIGN CHAR AND CALCULATE DELTA FREQ. + CURRENT
                ;HIGHER IN FREQ, - LOWER IN FRQ THEN INITAL READING.
                ;
02F9 FE00       SGNDEL:  CPI     00H       ;WAS INITAL > CURRENT
02FB CA1803              JZ      MINUS     ;IT WAS >
02FE 36FB                MVI     M,0FBH    ;"+" LESS 30H FOR PRINT ROUTINE
0300 23         SGNDEL1: INX     H         ;SET UP FOR DIGITS
0301 227012              SHLD    SAVE1     ;SAVE DBCD PNTR
0304 2A6E12              LHLD    SAVE      ;GET BACK LARGER # PNTR
0307 EB                  XCHG              ;AND PUT IN DE
0308 0E02       SGNDEL2: MVI     C,02      ;NUM DIGITS TO SUBT.
030A CD9901              CALL    SUB60     ;SUBTRACT INITAL,CURRENT
030D 2B                  DCX     H         ;BACK UP TO LSBYTE OF RESULT
030E 56                  MOV     D,M       ;PUT IN D
030F 2B                  DCX     H         ;NOW MSD
0310 5E                  MOV     E,M
0311 2A7012              LHLD    SAVE1     ;GET BACK DBCD PNTR
0314 CDC301              CALL    BINDEC    ;CNVT TO BCD AND STORE
0317 C9                  RET
                ;
0318 36FD       MINUS:   MVI     M,0FDH    ;"-" LESS 30H FOR PRT ROUTINE
031A C30003              JMP     SGNDEL1   ;RETURN WITH CORRECT FLAG.
                ;
                ;DELTA COMPARES OTTO AND HUMID INITAL AND CURRENT READINGS
                ;CALULATE SIGN, CONVERTS DELTAS TO BCD AND INSTALLS IN
                ;THE PRINT STRING FOR OUTPUT.
                ;
031D CD8202     DELTA:   CALL    INLBIN    ;CNVT ALL BCD READING TO BIN AND STORE
0320 CDB402              CALL    RDCMP     ;CMP O&H SIGN EACH PAIR AND UNCVT TO BCD
0323 C9                  RET
                ;
                ;
0324 2A6C12     VALID:   LHLD    DFBIN     ;GET LAST DIF
0327 227212              SHLD    LSTDF     ;SAVE IT
032A CD3F03              CALL    RRISE     ;IS RATE TO HIGH
032D FEFF                CPI     0FFH      ;FOR OTTO FUEL
032F CA7A03              JZ      NGRD      ;NO GOOD USE OLD READING
0332 CD4203              CALL    DIFF      ;SO CAL DIF OTTO-HUMID
0335 212F12     VALID1:  LXI     H,DMSD    ;PNT TO STORE DEC OF DIF
0338 CDC301              CALL    BINDEC    ;CNVRT TO DECIMAL
033B CD2802              CALL    PPM       ;CAL PPM AND STORE
033E C9                  RET
                ;
033F 3E00       RRISE:   MVI     A,00H     ;OK FLAG -A DUMMY
0341 C9                  RET
                ;
                ;ROUTINE TO TEST AND CAL DIFF OF OTTO AND HUMID
0342 112712     DIFF:    LXI     D,HDELT   ;PNT TO HUMID DELTA
0345 211F12              LXI     H,ODELT   ;PNT TO OTTO DELTA
0348 CD8803              CALL    TSTRD     ;TEST FOR VALID COND OF DELTAS
034B FEFF                CPI     0FFH      ;COND NG SO USE OLD READINGS
```

```
034D CA7A03              JZ     NGRD    ;IF WAS THEN RD NO GOOD
0350 FE3F                CPI    3FH     ;READING OK BUT ADD DIFS
0352 CAB403              JZ     DIFADD  ;ADD SIGNS DIF
0355 FEFB                CPI    OFBH    ;A PLUS?
0357 CA6F03              JZ     PLUS    ;THEN MODIFY SUB80 RET
035A 0E02                MVI    C,02    ;HL =SUBTRAHEND,&2 DIGITS
035C CD9901              CALL   SUB80   ;SUBTRACT
035F 1A        NEGAT:    LDAX   D       ;PNT TO RESULT OF SUB 80
0360 77                  MOV    M,A     ;HL PNT TO DFBIN
0361 23                  INX    H       ;NOW LO BYTE
0362 13                  INX    D
0363 1A                  LDAX   D       ;SAVE LO BYTE
0364 77                  MOV    M,A
0365 2A6C12   DIFF1:     LHLD   DFBIN   ;GET DFBIN
0368 EB                  XCHG
0369 3EFB                MVI    A,OFBH  ;A'+' LESS 30H
036B 323712              STA    PPMSD   ;PUT IN FLAG
036E C9                  RET
036F 0E02     PLUS:      MVI    C,2     ;2BYTE SUB
0371 CD9901              CALL   SUB80
0374 EB                  XCHG           ;PNT TO ANS
0375 1B                  DCX    D       ;LESS 2 LOCATIONS
0376 1B                  DCX    D
0377 C35F03              JMP    NEGAT   ;RET TO NORMAL ROUTINE
         ;
037A 217212   NGRD:      LXI    H,LSTOF ;PNT TO OLD READING
037D 5E                  MOV    E,M     ;PUT IN DE
037E 23                  INX    H
037F 56                  MOV    D,M
0380 3EFD                MVI    A,OFDH  ;A'-' LESS 30H
0382 323712              STA    PPMSD   ;PUT IN FLAG
0385 C33503              JMP    VALID1  ;GOTO PPM ROUTINE
         ;
0388 1A       TSTRD:     LDAX   D       ;HDELT
0389 BE                  CMP    M       ;ODELT
038A CA9503              JZ     TSTRD1  ;BOTH SAME SO CMP O&H
038D FEFD                CPI    OFDH    ;NOT SAME ,IS H-&O+
038F CAA903              JZ     NVALD   ;THEN NOT VALIID
0392 3E3F                MVI    A,3FH   ;FALL THRU H+&O-
0394 C9                  RET
         ;
0395 47       TSTRD1:    MOV    B,A     ;BOTH SAME SAVE FLAG
0396 116A12              LXI    D,HDBIN ;GET BIN OF HUMID
0399 216812              LXI    H,ODBIN ;OTTO
039C CD6502              CALL   DBCMP   ;WHICH IS BIGGER
039F FE00                CPI    0       ;OTTO?
03A1 CAAC03              JZ     OBIG    ;OTTO WAS
03A4 3EFB                MVI    A,OFBH  ;H>O BUT WAS IT +
03A6 B8                  CMP    B       ;BOTH =?
03A7 EB                  XCHG           ;GET READY FOR SUB80
03A8 C8                  RZ             ;OK LEAVE OFBH AS FLAG
03A9 3EFF    NVALD:      MVI    A,OFFH  ;SET NG FLAG
03AB C9                  RET
         ;
03AC 3EFD    OBIG:       MVI    A,OFDH         ;SIGN-
03AE B8                  CMP    B       ;WAS   OTTO -
03AF EB                  XCHG           ;SET UP FOR SUB80
03B0 C8                  RZ             ;O>H &BOTH -.SO OK
03B1 C3A903              JMP    NVALD   ;BOTH + SO NG
         ;
03B4 2A6A12   DIFADD:    LHLD   HDBIN   ;GET HUM
03B7 EB                  XCHG
03B8 2A6812              LHLD   ODBIN
```

```
03BB 19                     DAD     D           ;ADD H+O
03BC 226C12                 SHLD    DFBIN       ;SAVE IT
03BF C36503                 JMP     DIFF1                   ;GOTO BCD CONV
               ;
03C2 216C12     ALARM:  LXI     H,DFBIN     ;PNT TO DIF
03C5 7E                     MOV     A,M         ;GET LO BYTE
03C6 FE32                   CPI     MAXPPM      ;IS IT ABOVE MAX LEVEL
03C8 DADC03                 JC      OFF                     ;OK NO ALARM
03CB 3A7812                 LDA     PIAWRD      ;GET STAT WRD
03CE E620                   ANI     20H         ;ALARM ON?
03D0 C0                     RNZ                 ;IT IS, GO BACK
03D1 3A7812                 LDA     PIAWRD      ;GET BACK STAT
03D4 C620                   ADI     20H         ;NOPE
03D6 D3C1                   OUT     FDATAB      ;SO TURN ON
03D8 327812                 STA     PIAWRD      ;SAVE NEW STAT
03DB C9                     RET
               ;
03DC 3A7812     OFF:    LDA     PIAWRD      ;GET STAT
03DF E620                   ANI     20H         ;TST
03E1 C8                     RZ                  ;IT'S OFF ALREADY
03E2 3A7812                 LDA     PIAWRD      ;GET BACK STAT
03E5 D620                   SUI     20H         ;CLR BIT
03E7 D3C1                   OUT     FDATAB
03E9 327812                 STA     PIAWRD      ;SAVE STAT
03EC C9                     RET
               ;
03ED 214304     DISPLAY:    LXI     H,INTDS ;PNT TO INITALZN
03F0 CD2404                 CALL    DSPOUT  ;CLR DISPLAY
03F3 213C04                 LXI     H,CONC  ;PNT TO CONC MSG
03F6 CD2404                 CALL    DSPOUT  ;DISPLAY STRING
03F9 213A12                 LXI     H,PPMSD+3       ;PNT TO MSD
03FC 117E12                 LXI     D,PPMDSP        ;PNT TO TEMP STORE
03FF 0E02                   MVI     C,02    ;3 DIGIT TO DEC. PNT
0401 7E         DISPLA1:    MOV     A,M     ;GET 1ST DIGIT
0402 C630       DISPLA2:    ADI     30H     ;BLANK
0404 12                     STAX    D       ;STORE ASCII VALUE
0405 23                     INX     H
0406 13                     INX     D
0407 0D                     DCR     C       ;BUMP PNTRS
0408 C20104                 JNZ     DISPLA1 ;DO 3 DIGITS
040B 3E2E                   MVI     A,2EH
040D 12                     STAX    D       ;PUT IT IN
040E 7E                     MOV     A,M     ;GET IT
040F C630                   ADI     30H     ;MAKE IT ASCII
0411 13                     INX     D
0412 12                     STAX    D       ;STORE IT
0413 13                     INX     D
0414 3EFF                   MVI     A,0FFH  ;INSERT END OF STRING
0416 12                     STAX    D
0417 217E12                 LXI     H,PPMDSP        ;PNT TO VALUE STR
041A CD2404                 CALL    DSPOUT
041D 215004                 LXI     H,PPMSG ;END W/PPM
0420 CD2404                 CALL    DSPOUT
0423 C9                     RET
               ;
0424 7E         DSPOUT: MOV     A,M     ;GET CHR
0425 FEFF                   CPI     0FFH    ;IS IT END OF STR
0427 C8                     RZ
0428 D320                   OUT     DDATAA  ;SET THE DATA
042A 3E01                   MVI     A,1     ;STROBE IT
042C D322                   OUT     DDATAC
042E CD7501                 CALL    WAIT
```

```
0431 3E00            MVI     A,0
0433 D322            OUT     DDATAC
0435 CD7501          CALL    WAIT
0438 23              INX     H
0439 C32404          JMP     DSPOUT  ;LOOP TILL DONE
                ;
043C 20434F4E43CONC: DB      20H,43H,4FH,4EH,43H,20H,0FFH
0443 8B706E6D6BINTDS:DB      8BH,70H,6EH,6DH,6BH,68H,67H,65H,62H,61H,8AH,00H,0FFH
0450 2050504D20PPMSG:DB      20H,50H,50H,4DH,20H,0FFH
0456 204155544FZERO: DB      ' AUTO-ZEROING ',0FFH
0465 2046415354FSMSG:DB      ' FAST ZEROING ',0FFH
                ;
0474 F5      FAST:   PUSH    PSW     ;SAVE REG
0475 E5              PUSH    H
0476 D5              PUSH    D
0477 C5              PUSH    B
0478 3A7812          LDA     PIAWRD
047B C650            ADI     50H     ;TURN ON VALVE AND PUMP
047D 327812          STA     PIAWRD  ;SAVE STAT
0480 D3C1            OUT     FDATAB  ;TURN ON PUMP
0482 214304          LXI     H,INTDS ;CLR DISPLAY
0485 CD2404          CALL    DSPOUT
0488 216504          LXI     H,FSMSG ;FAST-ZEROING
048B CD2404          CALL    DSPOUT
048E 210001          LXI     H,0100H ;APROX 25SEC WAIT
0491 CD7501  FSLOP:  CALL    WAIT
0494 2D              DCR     L
0495 C29104          JNZ     FSLOP
0498 25              DCR     H
0499 C29104          JNZ     FSLOP
049C CD2301          CALL    START6  ;ZERO INITAL
049F 3A7812          LDA     PIAWRD  ;GET STAT
04A2 D610            SUI     10H     ;OPEN VALVE
04A4 327812          STA     PIAWRD
04A7 0603            MVI     B,03    ;DO 10 SEC COUNT
04A9 CDE900          CALL    START5  ;DISPLAY
04AC 217C12          LXI     H,FSCNT ;PNT TO FAST CNTR
04AF 3610            MVI     M,10H   ;FAST RUN FOR 3 MIN
04B1 0601    FAST1:  MVI     B,01
04B3 CDE900          CALL    START5
04B6 217C12          LXI     H,FSCNT ;LOOP FOR 3 MIN
04B9 35              DCR     M
04BA C2B104          JNZ     FAST1
04BD 214304          LXI     H,INTDS ;CLR DISPLAY
04C0 CD2404          CALL    DSPOUT
04C3 216A04          LXI     H,FSMSG+5       ;ZEROING MSG
04C6 CD2404          CALL    DSPOUT
04C9 C3EE04          JMP     FASTED  ;DO A REZERO
                ;
                ;
04CC F5      AUTOZ:  PUSH    PSW
04CD E5              PUSH    H
04CE D5              PUSH    D
04CF C5              PUSH    B
04D0 3E50            MVI     A,50H   ;FAST PUMP AND VALVE
04D2 D3C1            OUT     FDATAB
04D4 214304          LXI     H,INTDS ;INTAL DISPLAY
04D7 CD2404          CALL    DSPOUT
04DA 215604          LXI     H,ZERO  ;AUTOZERO MESS.
04DD CD2404          CALL    DSPOUT
04E0 217F03          LXI     H,037FH ;WAIT 90 SEC
04E3 CD7501  AUTOZ1: CALL    WAIT
04E6 2D              DCR     L
```

```
04E7 C2E304             JNZ     AUTOZ1
04EA 25                 DCR     H
04EB C2E304             JNZ     AUTOZ1
04EE 3E10      FASTED:  MVI     A,10H
04F0 D3C1               OUT     FDATAB  ;SLOW PUMPING
04F2 212C01             LXI     H,012CH ;WAIT FOR 30 SEC MORE
04F5 CD7501    AUTOZ2:  CALL    WAIT
04F8 2D                 DCR     L
04F9 C2F504             JNZ     AUTOZ2
04FC 25                 DCR     H
04FD C2F504             JNZ     AUTOZ2
0500 0603               MVI     B,03
0502 CD2301             CALL    START6
0505 CDE900             CALL    START5
0508 3E00               MVI     A,0     ;CLR ALL
050A 327212             STA     LSTDF   ;SET LSD TO ZERO
050D 327312             STA     LSTDF+1 ;ZERO HI BIT
0510 327812             STA     PIAWRD  ;SAVE STAT
0513 D3C1               OUT     FDATAB
0515 C1                 POP     B
0516 D1                 POP     D
0517 E1                 POP     H
0518 F1                 POP     PSW
0519 FB                 EI              ;RESET INTR
051A C9                 RET
          ;
```

APPENDIX B - COMPUTER PROGRAM FLOW CHART

SUBROUTINES CALLED BY AND LINEAR SEGMENTS USED BY THE MAIN LOOP
================================================================

INIT:
-----

Set mode port C: Bits 0-3 control Freq. cntr; 4-5 MUX of same
                              :
                              v
Set mode port B: Bits 0-3 BCD in; 4-7 control ALARM,PUMP,AZ valve
                              :
                              v
                        Set up STACK
                              :
                              v
    Set mode port A: Bits 0-7 Digit select of frequency counter
                              :
                              v
      Set mode port A: Bits 0-7 Alpha-meric display data output
                              :
                              v
        Set mode port C: Bit 0 Panel display output strobe
                              :
                              v
                      Enable RESTART A,B,C
                              :
                              v
                    Install Restart Vectors
                              :
                              v
              Initialize Alpha-meric panel display

```
                              :
                              :
                              v
                       (on to START:)
      ROUTINES CALLED FROM MEASUREMENT LOOP STARTS:
      ==================================================

RDOSC:
                            ------

Reset the frequency counter
                              :
                              v
           Switch the multiplexer to correct input
                              :
        ---------------->:
         ^                    v
         :             Input status port
         :                    :
         :        no          v
         :--------------Test for store
         :                    :--yes
      -------------------------->:
      ^  ^                       v
      :  :          Input digit enable data
      :  :                       :
      :  :      no               v
      :  -----------Test for correct digit
      :                          :--yes
      :                          v
      :                     Get BCD data
      :                          :
      :                          v
      :                    Mask 4 L.S. Bits
      :                          :
      :                          v
      :                 Store digit in memory
      :                          :
      :                          v
      :               Increment memory pointer
      :                          :
      :                          v
      :              Get back last digit pointer
      :                          :
      :                          v
      :         Rotate the word to point to next digit
      :                          :
      :                          v
      :               Save the new digit pointer
      :                          :
      :                no        v
      :----------------------Test if last digit
                                 :
                                 :-yes
                                 v
                             (RETURN)

VALID:  Routine to test rate of rise, test sign of dFreq.for Otto
   and Humidity sensors, calculate PPM if conditions are correct, if
                 not, use last valid reading.
                 ==============================
```

DELTA: Routine to calculate changes in frequency of Otto and
       Humidity oscillators, determine valid changes.
       ==================================================

```
                              DELTA:
                              ------

Set pointers for BCD and store for binary of same  -INLBIN:
                                 :
                                 v
    Set up registers for conv'n and sequential processing   -RDCNVT:
                                 :
                                 v
                Do B.C.D. to binary conversion              -CNVRT:
                                 :
                                 v
     Set up pntrs for comparison of initial and current     -RDCMP:
                                 :
                                 v
      Do DB compare of init. and curr. reading pnt to larger -DBCMP:
                                 :
                                 v
 Determine direction of change, set up for correct subt'n   -SGNDEL:
                                 :
                                 v
                Do double precision subtract                -SUB80:
                                 :
                                 v
       Reconvert BIN to BCD and install in print line       -BINDEC:
                                 :
                                 v
      Repeat above sequence for Otto, Humidity, and Ref.
                                 :
                                 v
                           (on to PPM:)
                              VALID:
                              ------

Test for rate of rise                  -RRISE:
                                 :
                                 v
 Set up pntrs for calculation of difference of dFreq.s      -DIFF:
                                 :
                                 :
 Conditons NG                    v
 -------------< Test for sign of both dFrequencies          -TSTRD:
  :                              :
  :       Add                    :-conditions OK
  :       ------<Are th: differences to be Add or Subt
  :       :            •.        :
  :       :                      :-Subtract
  :       :                      :
  :  ADD dFs -DIFADD:    Subtract Differences               -SUB80:
  :       :                      :
  :       ------------------------>:
  :                              :
  ---Use last Difference--------->:
```

```
                              :
                              v
                  Save Difference and sign
                              :
                              v
       Convert to decimal and install in print line  -VALID1:
                              :
                              v
                        (on to PPM:)
PPM:   Routine  to convert the difference of the reading into  PPM
of Otto Fuel.  Based on a two segment straight line fit  breaking
at 1.0 PPM Otto fuel.  From 0.0 to 1.0 having a slope of 10Hz/PPM
and above 1.0 PPM an intercept of 38Hz and a slope of 6Hz/PPM.
==================================================================

PPM:
                            ----

Load registers with difference
                              :
                              :
                              :
                              v
                 Load the ten times Low PPM Slope
                              :
                              :
                              :
0-1PPM                        v                         1 plus
--------< Test if 0-1PPM or 1 plus PPM Otto fuel-----
   :                                                       :
   :                                                       :
   :                                                       :  -GRT1:
use LPPM divisor                                   Subt.intercept
   :                                                       :
   :                                                       :
   :                                                use HPPM divisor
   :                                                       :
   :                                                       :
   ---------------------------->:<-----------------------
                              :
                              :
               Divide the difference by the slope        -DIV80:
                              :
                              :
                              v
              Do binary to decimal conversion           -BINDEC:
                              :
                              :
                              v
                       (on to ALARM:)

ALARM: Routine to sound the alarm if the PPM > 0.7PPM
   ==============================================================
```

```
                        ALARM:
                        ------

Recover the Binary value of PPM
                           :
                           :
                           v
               Get Maximum value of PPM
                           :
                           :
      no alarm             v
    --------------< Compare the values
    :                      :
    :                      :
    :                      :-yes alarm
    :                      :
    :                      v
    :          Load PIA word to turn on ALARM
    :                      :
    :                      :
    :                      v
    :            Output to PIA- on alarm
    :                      :
    ----------------------->:
                           :
                           :
                           v
                Reset the  PIA status word
                           :
                           :
                           v
                   (on to DISPLAY:)
```

DISPLAY: Routine to Clear display and indicate the current PPM
value. Prints value, CONC PPM message, refresh interval 10Sec.
================================================================

```
                       DISPLAY:
                       --------

Set pointers to clear screen string
                           :
                           :
                           v
                    Print the string
                           :
                           :
                           v
                  Point to PPM digits
                           :
                           :
                           v
                    Print the string
                           :
                           :
                           v
```

Point to the CONC PPM. string
:
:
v
Print the string
:
:
v
(on to PRINT)

NB in the PROM version without monitor, the PRINT routine is not operative.

AZERO: Routine to automatically zero the instrument after a predetermined interval.
=========================

AZERO:
------

Save all registers
:
:
v
Turn on switch for high speed pumping
Switch the value to connect second Otto fuel trap in series with the main inlet to the monitor
:
:
v
Clear the display
:
:
v
Print the "AUTO-ZEROING" message
:
:
v
Wait for 90 second interval
:
:
v
Switch to slow (normal) pumping
:
:
v
Wait for 30 seconds more
:
:
v
Do initial set of readings
:
:
v
Do a set of current readings and display
:
:

```
                                   v
      Zero last difference value, set PIA word restore registers
                                   :
                                   :
                                   v
                               (RETURN)
FAST: Routine for high speed pumping. Pumping interval is 3 min.
      Interval is preceded by auto-zeroing.
      =========================================

FAST: -
                              -----

Save all registers
                                   :
                                   :
                                   v
       Switch in Azero trap and go to high speed pumping
                                   :
                                   :
                                   v
              Clear display and print FAST-ZEROING
                                   :
                                   :
                                   v
                         Wait for 25 seconds
                                   :
                                   :
                                   v
                      Do set of initial Readings
                                   :
                                   :
                                   v
              Open valve and do set of current readings
                                   :
                                   :
                                   v
 Loop  for  interval of 3 min.  w/high speed pumping while  making
    measurements and displaying the concentration of Otto fuel.
                                   :
                                   :
                  Clear the display and print ZEROING
                                   :
                                   :
                                   v
  Jump to  the final segment of AUTO-ZEROING routine  -FASTED:
      finish with low speed pumping and the instrument zeroed
                                   :
                                   :
                                   v
                Restore registers, enable interrupts
                                   :
                                   :
                                   v
                               (RETURN)
```

AUTO-ZERO Feature

Description:

The auto-zero feature of the monitor allows for the periodic re-zeroing of the instrument to adjust for the gradual aging and/or contamination of the crystals and any other condition which could affect the base operating frequencies of the dual detector oscillators.

To re-zero a unit without this automatic mode would require that a manual zeroing cycle be done in an environment completely free of Otto fuel vapours. To ensure such a condition, it is likely, that being out-of-doors would be the only suitable and and practical place to carry out a re-zeroing.

A better option is to automatically connect an additional trap for Otto fuel between the inlet and the main gas line which would "scrub-out" any fuel and allow "clean" air to be drawn through the unit while a programmed sequence of pumping rates and measurement intervals was executed. During this time a new set of base frequency measurements for both the sample and reference oscillators would be made and stored. From these base frequencies and the any changes in frequency caused by Otto fuel during a future measurement cycle, a precise determination of Otto fuel concentration can be calculated.

The embodiments of the invention in which an exclusive property or priviledge is claimed are defined as follows:

1. A method of determining the concentration of a vapour in a gaseous fluid, comprising the steps of:
   maintaining the temperature of samples of said gaseous fluid within a predetermined temperature range;
   passing a first sample of said fluid through a first channel having a first crystal oscillator therein coated with a substance capable of reversibly absorbing said vapour;
   simultaneously passing a second sample of said fluid through a second channel having a filter therein for removing said vapour from said second sample and a second crystal oscillator therein coated with a substance capable of reversibly absorbing said vapour;
   monitoring the difference in the frequencies of said first and second osillators; and
   converting the difference in said frequencies, if any, to a numerical value indicative of the concentration of said vapour in said fluid.

2. A method as defined in claim 1, further including the step of passing each said sample through a heat exchanger to preheat said samples to a predetermined temperature.

3. A method as defined in claim 1, said vapour being Otto Fuel II and said substance being dicyanoallysilicone.

4. A method as defined in claim 3, said filter being formed of cellulose acetate butyrate.

5. A device for detecting the concentration of a vapour in a gaseous fluid, said device comprising:
- a fluid manifold having an inlet passage for admitting fluid thereinto and an outlet passage for discharging fluid therefrom;
- a reference fluid channel having a fluid inlet end in fluid communication with said fluid inlet passage and an outlet end in fluid communication with said manifold outlet passage, said channel having filter means therein for removing said vapour from fluid flowing through said channel;
- a measuring fluid channel having a fluid inlet end in fluid communication with said fluid inlet passage and an outlet end in fluid communication with said manifold outlet passage;
- a reference crystal oscillator adapted to oscillate in a vapour free environment at a predetermined base-line frequency disposed in said reference channel, said crystal being coated with a substance adapted to reversibly absorb said vapour and being operable to produce a first signal at a frequency representative of the concentration of vapour in the fluid passing through said reference channel;
- a measuring crystal oscillator adapted to oscillate in a vapour free environment at substantially said predetermined base-line frequency disposed in said measuring channel, said measuring crystal being coated with a substance adapted to reversibly absorb said vapour and being operable to produce a second signal at a frequency representative of the concentration of vapour in the fluid passing through said reference channel; and
- means responsive to the difference between the frequency of said first and second signals for producing a third signal representative of the numerical value of said concentration of vapour flowing through said second channel and displaying the value of said concentration on a display.

6. A device as defined in claim 5, further including alarm means responsive to a third signal indicating a vapour concentration exceeding a predetermined value.

7. A device as defined in claim 5, further including heat exchanger means disposed in said manifold upstream of said reference and measuring channel for maintaining the fluid fed to said channels with a predetermined temperature range.

8. A device as defined in claim 7, said heat exchanger being an electrical resistance heater.

9. A device as defined in claim 5, said manifold further including first and second fluid passages disposed in parallel with one another upstream of said channel, each said passage having an inlet end in fluid communication with said inlet passage and an outlet end in fluid communication with each said channels, valve means at the outlet ends of said passages for selectively communicating one of said passages with said channels, and filter means in one of said passages for removing said vapour from a fluid stream flowing therethrough.

10. A device as defined in claim 5, said responsive means including electrical circuit means for monitoring the output of said crystal oscillators.

11. A device as defined in claim 10, said circuit means including a microprocessor.

12. A device as defined in claim 11, said circuit means including a display for displaying under the control of said microprocessor a numerical value of the concentration of said vapour in said fluid.

13. A device as defined in claim 5, said vapour being Otto Fuel II and said substance being dicyanoallysilicone.

14. A device as defined in claim 13, said filter means in said reference channel being a tube formed of cellulose acetate butyrate.

15. A device as defined in claim 5, said manifold having a plurality of additional measuring channels, each said additional channels being in parallel with said reference and the first mentioned measuring channel and having disposed therein a crystal of an oscillator, said crystals disposed in said measuring channels being coated with different substances, each capable of reversibly absorbing at least one particular vapour of interest and each said oscillator being connected to said responsive means.

16. A device as defined in claim 15, wherein said substances include one or more of the group consisting of Apiezon H TM for detecting Distillate and Freon 12, Apiezon M TM for detecting Distillate, Tricresylphosphate for detecting Otto Fuel and Dicyanoallylsilicone for detecting Otto Fuel.

17. A device as defined in claim 5, each said oscillator having an uncoated nominal frequency 10 MHz, said substance being uniformly distributed over said crystals to a depth which produces a negative frequency shift in the range of approximately 50 to 60 kHz when said oscillators are operated in a vapour free environment.

18. A device as defined in claim 17, said vapour being Otto Fuel II and said substance being dicyanoallysilicone.

19. A device as defined in claim 18, said filter means in said reference channel being a tube formed of cellulose acetate butyrate.

20. A device for detecting the concentration of Otto Fuel II in ambient air, said device comprising:
- a housing having an inlet passage for admitting gaseous fluid into said housing and an outlet passage for discharging fluid from said housing;
- a particulate filter disposed in said fluid inlet passage for removing particulate material from fluid entering said fluid inlet;
- a first pair of parallel fluid passages, each passage of said pair of passages having an inlet end connected to said fluid inlet passage, one of said passages having filter means therein for removing Otto Fuel II from fluid flowing through said one of said passages;
- computer controllable valve means connected to the outlet end of each said passage of said pair of passages for selectively communicating one of said passages with said fluid outlet passage;
- heat exchanger means, for maintaining fluid flowing therethrough within a predetermined temperature range, said heat exchanger means having an inlet end in fluid communication with said valve means and an outlet end;
- a reference fluid channel having a fluid inlet end in fluid communication with the outlet end of said heat exchanger means and an outlet end in fluid communication with said housing outlet passage, said channel having filter means therein for removing Otto Fuel II from fluid flowing through said channel;
- a measuring channel having a fluid inlet end in fluid communication with the outlet end of said heat exchanger means and an outlet end in fluid communication with said housing outlet passage;
- electrical circuit means including:

a reference quartz piezoelectric crystal adapted to oscillate at a predetermined base-line frequency disposed in said reference channel, said crystal having a coating thereon adapted to absorb Otto Fuel II, said reference crystal being operable to produce a first signal at a frequency representative of the concentration of Otto Fuel II in the fluid passing through said reference channel;

a measuring quartz piezoelectric crystal adapted to oscillate at substantially said predetermined base-line frequency disposed in said measuring channel, said measuring crystal having a coating thereon adapted to absorb Otto Fuel II, said measuring crystal being operable to produce a second signal at a frequency representative of the concentration of Otto Fuel II in the fluid passing through said reference channel;

a multiplexer connected to each said crystal for receiving said first and second signals;

a frequency counter connected to said multiplexer for producing a first and second additional signals representative of the frequency of each said crystal;

microprocessor means for comparing said first and second additional signals and producing a signal representative of the concentration of Otto Fuel II flowing through said measuring channel, displaying said concentration on an alpha-meric display, and activating an alarm when said concentration exceeds a predetermined value.

* * * * *